United States Patent [19]

Zabransky

[11] 3,972,957
[45] Aug. 3, 1976

[54] HF ALKYLATION REACTION TEMPERATURE CONTROL SYSTEM

[75] Inventor: Robert F. Zabransky, Oak Brook, Ill.

[73] Assignee: Universal Oil Products Company, Des Plaines, Ill.

[22] Filed: June 20, 1975

[21] Appl. No.: 588,999

Related U.S. Application Data

[60] Division of Ser. No. 534,398, Dec. 19, 1974, which is a continuation-in-part of Ser. No. 468,956, May 10, 1974, abandoned.

[52] U.S. Cl. .................. 260/683.48; 208/DIG. 1; 235/151.13
[51] Int. Cl.² ........................................ C07C 3/54
[58] Field of Search ............ 260/683.48; 208/DIG. 1

[56] References Cited
UNITED STATES PATENTS

| | | | |
|---|---|---|---|
| 2,881,235 | 4/1959 | Van Pool | 260/683.48 |
| 2,929,857 | 3/1960 | Hutto | 260/683.48 |
| 2,990,437 | 6/1961 | Berger | 260/683.48 |
| 3,002,818 | 10/1961 | Berger | 260/683.48 |
| 3,018,310 | 1/1962 | Van Pool | 260/683.48 |
| 3,200,833 | 8/1965 | Phillips | 260/683.48 |
| 3,463,613 | 8/1969 | Fenske et al. | 208/DIG. 1 |
| 3,751,229 | 8/1973 | Bajek et al. | 208/DIG. 1 |
| 3,937,749 | 2/1976 | Zabransky | 260/683.48 |

Primary Examiner—G. J. Crasanakis
Attorney, Agent, or Firm—James R. Hoatson, Jr.; Robert W. Erickson; William H. Page, II

[57] ABSTRACT

A control system for regulating the reaction zone temperature in a process for the acid-catalyzed alkylation of an isoparaffin with a mixed olefinic feed stream. Composition characteristics of the liquid alkylate product and the olefinic feed stream are determined, and representative output signals transmitted to computer/comparator means which generates a computer output signal in response to, and as a function thereof. The computer output signal is employed to adjust the reaction zone temperature, for a given olefinic feed composition, in order to maximize the octane rating of the liquid alkylate product. The control system effects rapid compensation for feed composition changes which would otherwise adversely affect the product octane rating.

6 Claims, 1 Drawing Figure

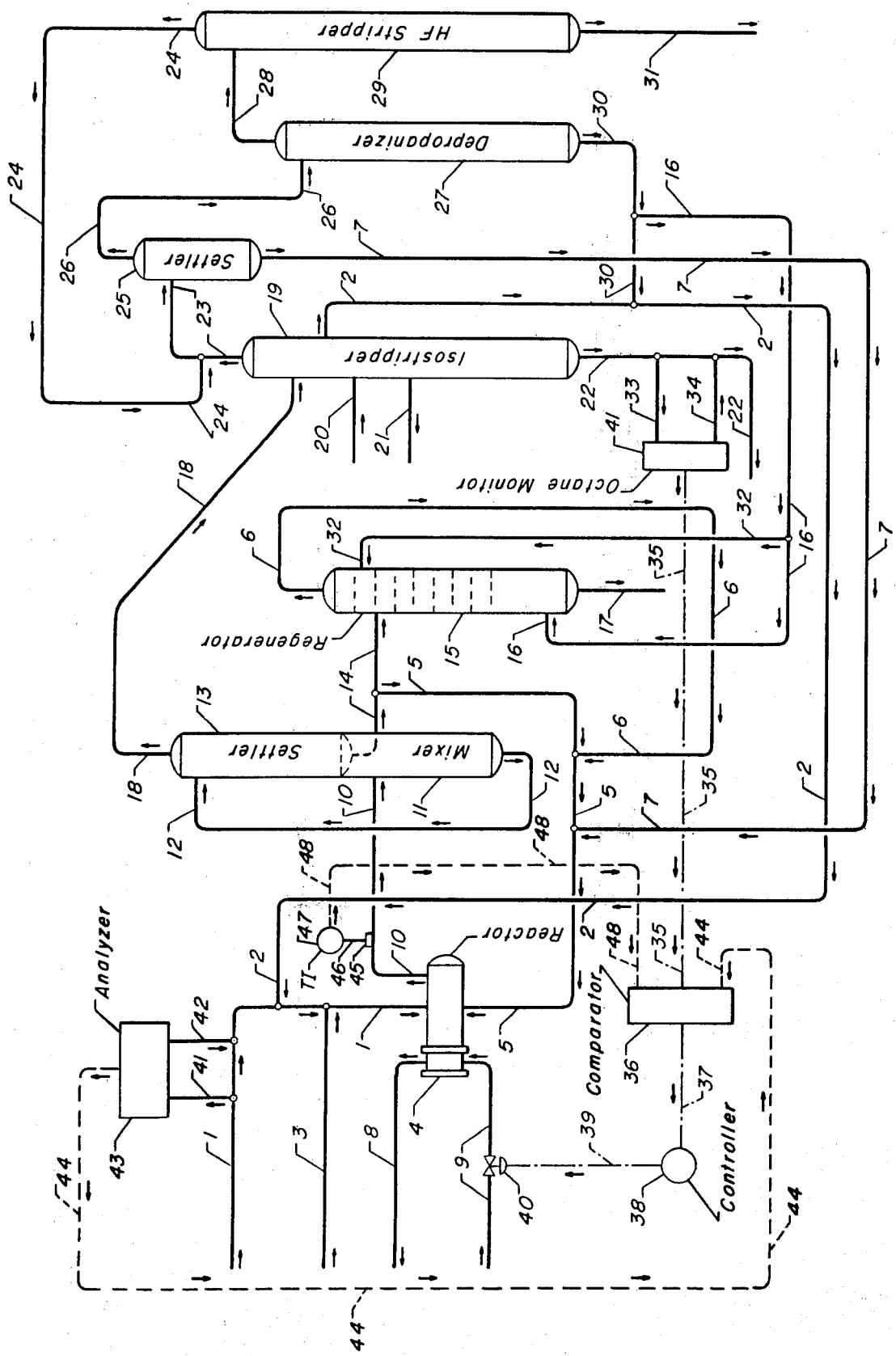

:

HF ALKYLATION REACTION TEMPERATURE CONTROL SYSTEM

RELATED APPLICATIONS

This application is a Division of my copending application, Ser. No. 534,398, filed Dec. 19, 1974, which copending application constitutes a Continuation-In-Part of my copending application Ser. No. 468,956, filed May 10, 1974 and now abandoned, all the teachings of which applications are incorporated herein by specific reference thereto. The present application is filed to comply with a requirement for restriction in Ser. No. 534,398.

APPLICABILITY OF INVENTION

The control system herein described is intended for utilization in a process for the production of a normally liquid alkylate product via the reaction of an isoparaffin with an olefin. Although intended for use in any acid-catalyzed alkylation process — e.g. sulfuric acid alkylation — my invention is most applicable to alkylation processes effected in contact with a hydrogen fluoride catalyst. For more than a quarter of a century, the demand for high-octane fuels, possessing enhanced anti-knock characteristics, has increased at a staggering rate. These improved fuels are required in voluminous quantities to satisfy the ever-accelerating degree of motor fuel consumption. Within the petroleum industry, various processes have been developed which have proved successful in alleviating the intertwined problems attendant supply, quality and demand. Among the first of such processes was the acid-catalyzed alkylation of an isoparaffin with an olefin, both generally normally vaporous, to produce a higher molecular weight, normally liquid isoparaffin. Since isoparaffins, in contrast to normal paraffins, possess significantly higher octane ratings and blending values, and thus improve the anti-knock properties of the motor fuel, processes capable of efficiently effecting such a reaction have gained wide acceptance within the petroleum industry. For many economic and technical reasons, well known to those having the requisite skill in the appropriate art, the alkylation process catalyzed by a hydrogen fluoride catalyst predominates. HF alkylation of an isoparaffin with an olefin has, since the advent thereof, experienced a multitude of changes and improvements with respect to unit design and/or operating techniques. The process and control system encompassed by my inventive concept also constitutes an improvement which affords enhanced operational stability, while simultaneously providing economic advantages.

Although applicable to the alkylation of an olefinic hydrocarbon having from about 3 to about 7 carbon atoms per molecule, with an isoparaffin having from about 4 to about 7 carbon atoms per molecule, the present control system is uniquely advantageous in those processes where isobutane is alkylated with an olefinic feed stream containing at least two olefins selected from the group consisting of propylene, 1-butene, 2-butene and isobutylene. Therefore, in the interest of brevity, further description of the control system and alkylation process will be directed toward the HF-catalyzed alkylation of isobutane with mixed olefins having three or four carbon atoms per molecule. Many processes which are integrated into an overall petroleum refining operation result in product streams containing significant quantities of the lower molecular weight olefinic hydrocarbons. Principal among such processes is the well known fluid catalytic cracking process; other processes include thermal cracking, or pyrolysis units, coking operations and visbreaking. The olefinic feed streams from one or more of these processes are generally recovered by way of gas concentration facilities which are specifically intended to concentrate the $C_3$- and $C_4$-olefins. Exemplary of such mixed olefin concentrates is one containing about 51.3% by volume propylene, 48.2% by volume of mixed butylenes and about 0.5% by volume of mixed amylenes.

Investigations have indicated that the quality of the normally liquid alkylate product is, at a selected reaction zone pressure, dependent upon the temperature at which the reaction mixture is maintained within the reaction zone. Since the acid-catalyzed alkylation process is exothermic, temperature control of the reaction mixture, via indirect heat exchange with a suitable cooling medium, has been, and continues to be a commonly-practiced technique. This relatively simple temperature control system will suffice where the feed stream is a substantially pure olefinic hydrocarbon. However, the olefinic feed streams in virtually 100% of the acid-catalyzed alkylation processes constitute mixtures of two or more of the aforementioned olefinic hydrocarbons. This contributes a degree of complexity with respect to temperature control of the reaction mixture. Considering, for the sake of illustration, substantially pure olefinic feed streams, the quality of the alkylate produced from 1-butene is improved by increasing the reaction temperature, while that produced from either 2-butene, or isobutylene is improved by decreasing the temperature of the reaction mixture. Additionally, a higher quality alkylate product is produced from a propylene feed stream at higher temperatures than those which are optimum for the alkylation of $C_4$-olefins. Since the character of the olefinic feed stream is dependent upon other units within the overall refinery, which units are subject to their own peculiar operating parameters, the composition of the olefinic feed stream introduced into the alkylation system is constantly changing.

The control system of the present invention affords a method for effecting the rapid compensation of feed stream composition changes with respect to the quality of the normally liquid product. There is afforded an enhancement of the steady-state operation of the system, particularly with respect to the stability of alkylate product quality, as well as the economic advantages attendant an increase in operational efficiency.

OBJECTS AND EMBODIMENTS

A principal object of the present invention is to afford an improvement in the hydrogen fluoride-catalyzed alkylation of olefinic hydrocarbons. A corollary objective is to enhance the character of steady-state operation attendant the alkylation of a normally vaporous isoparaffin with a normally vaporous olefinic hydrocarbon to produce a normally liquid alkylation product.

A specific object of my invention involves the control of reaction zone temperature when alkylating an isoparaffin with a mixed olefinic feed stream.

Therefore, one embodiment of my invention provides a control system for use in a process for alkylating an isoparaffin with an olefinic feed stream, to produce a normally liquid alkylate product, wherein said feed stream (1) contains at least two olefinic hydrocarbons and, (2) is contacted in admixture with a hydrocarbon fluoride catalyst, in a reaction zone, which control system, for regulating the temperature within said reaction zone, comprises, in cooperative combination: (a) conduit means for introducing a cooling medium into said reaction vessel, and for removing it therefrom, said cooling medium indirectly contacting the reaction mixture within said vessel; (b) flow-varying means for adjusting the flow of said cooling medium into said reaction zone; (c) a first hydrocarbon analyzer receiving a sample of said olefinic feed stream and developing a first process output signal representative of a composition characteristic of said olefinic feed stream; (d) temperature-sensing means for sensing a reaction zone temperature, and, operatively associated therewith, temperature-indicating means developing a second process output signal representative of said temperature; (e) a second hydrocarbon analyzer receiving a sample of said normally liquid alkylate product and developing a third process output signal representative of a composition characteristic of said sample; (f) process signal-transmitting means through which said three process output signals are transmitted to computer/comparator means developing a computer output signal in response to, and as a function of said three process output signals; and, (g) computer output signal-transmitting means through which said computer output signal is transmitted to said flow-varying means, whereby the flow of said cooling medium is adjusted in response thereto.

In another embodiment, my inventive concept encompasses a process for alkylating an isoparaffin with an olefinic feed stream, containing at least two olefins, which process comprises the steps of: (a) reacting said isoparaffin with said feed stream, in admixture with a hydrogen fluoride catalyst, in an alkylation reaction zone, at alkylating conditions resulting in a reaction product effluent containing normally liquid alkylate; (b) regulating the temperature of the reaction mixture, within said reaction zone, through indirect contact therein with a cooling medium, the flow of which is adjusted by flow-varying means; (c) introducing a sample of said olefinic feed stream into a first hydrocarbon analyzer and developing therein a first process output signal representative of a composition characteristic of said olefinic feed stream; (d) sensing a temperature of said reaction zone and developing a secnd process output signal representative thereof; (e) recovering said normally liquid alkylate from said product effluent; (f) introducing a sample of said alkylate into a second hydrocarbon analyzer and developing therein a third process output signal representative of a composition characteristic of said sample; (g) transmitting said three process output signals to computer/comparator means and developing therein a computer output signal in response to, and as a function of said three process output signals; and, (h) transmitting said computer output signal to said flow-varying means, whereby the flow of said cooling medium is adjusted in response thereto.

Other objects and embodiments will become apparent from the following additional description of the present inventive concept and the control system encompassed thereby, as well as from the description of the accompanying drawing. In one such other embodiment, the temperature-sensing means senses the temperature of the alkylation reaction zone effluent as it emanates therefrom. Similarly, the reaction vessel may be designed and constructed to provide an interior thermowell in order to sense the temperature within said vessel.

PRIOR ART

Candor compels recognition and acknowledgment of the fact that the prior art is replete with a wide variety of publications, inclusive of issued patents, directed toward the acid-catalyzed alkylation of an isoparaffin with an olefin. This is particularly true with respect to hydrogen fluoride alkylation which traces its development over an approximate 30-year period. Any attempt herein to exhaustively delineate the hydrogen fluoride alkylation art would constitute an exercise in futility. However, it is believed that a brief description of several innovations, for the purpose of illustrating the utilization of the present improvement and control system, will serve to define the area to which the technique is particularly applicable.

U.S. Pat. No. 3,560,587 (Cl. 260-683.48) describes the hydrogen fluoride alkylation of an isoparaffin/olefin mixture in a system which incorporates a reaction cooler, reaction soaker and a hydrogen fluoride acid-settler. The greater proportion of the hydrogen fluoride phase, separated within the settler, is recycled to the cooled reaction zone for further contact with the reactant mixture.

U.S. Pat. No. 3,686,354 (Cl. 260-683.43) is fairly illustrative of a complete hydrogen fluoride alkylation system including reaction vessels, reaction effluent separation for acid recovery and product separation for the recovery of the normally liquid alkylate product. In this system, the alkylate product is separated into a relatively high-octane fraction and a relatively low-octane fraction, the latter being further treated with additional isoparaffin and hydrogen fluoride catalyst. The present control system is intended for utilization in HF-catalyzed alkylation processes of the type above illustrated.

The integration and utilization of sophisticated control systems in a petroleum refining process are generally considered to be among recent technological innovations. In this respect, the published literature is slowly developing its own field of art. For example, U.S. Pat. No. 3,759,820 (Cl. 208-64) discloses the systematized control of a multi-reaction zone process in response to two different quality characteristics of the ultimately desired product. U.S. Pat. No. 3,649,202 (Cl. 23/253 A) involves the control of reaction zone severity in response to the octane rating of the normally liquid product effluent, and is primarily directed toward the well known catalytic reforming process.

As hereinbefore stated, the present control system is utilized to alleviate the problems attendant reaction zone temperature control in an acid-catalyzed alkylation process wherein an isoparaffin is alkylated with a mixed olefinic feed stream. The difficulties arising out of the utilization of an olefinic feed stream containing ever-varying concentration of propylene, 1-butene, 2-butene and isobutylene do not appear to be recognized either in the appropriate alkylation art, or in the control system published literature.

SUMMARY OF INVENTION

My invention is directed toward an improvement in the control of reaction zone temperature while alkylating an isoparaffin/olefin reactant stream. Although particularly applicable to the alkylation of isobutane with a butylene-containing olefinic stream, the process is also adaptable for utilization with other isoparaffinic and olefinic feed stocks for the purpose of producing motor fuel or aviation alkylates. Suitable isoparaffinic hydrocarbons are those having from about four to about seven carbon atoms per molecule, including isobutane, isopentane, neopentane, one or more of the isohexanes and various branched-chain heptanes. Similarly the olefinic reactant contains from about three to about seven carbon atoms per molecule, and includes propylene, 1-butene, 2-butene, isobutylene, the isomeric amylenes, hexenes, and various heptenes.

The alkylation reaction mixture comprises hydrogen fluoride catalyst, an isoparaffin and a mixed olefinic feed stream. With respect to the latter, the feed stream contains at least two olefinic hydrocarbons selected from the group consisting of propylene, 1-butene, 2-butene and isobutylene. The hydrogen fluoride catalyst is utilized in an amount generally sufficient to provide a catalyst/hydrocarbon volume ratio, within the reaction zone, of from about 0.5 to about 3.0. Hydrogen fluoride, as utilized throughout the present specification and appended claims, is intended to include catalysts where hydrogen fluoride is the active ingredient. As a general practice, commercial anhydrous hydrogen fluoride will be charged to the alkylation system as fresh catalyst. It is possible to use hydrogen fluoride containing as much as about 10.0% water; however, excessive dilution with water is undesirable since it tends to reduce the alkylating activity of the catalyst and introduces severe corrosion problems into the system. In order to reduce the tendency of the olefinic portion of the hydrocarbon feedstock to undergo polymerization prior to alkylation, the molar proportion of the isoparaffin to olefinic hydrocarbons within the alkylation reaction zone is maintained at a value greater than about 1.0:1.0, up to about 20.0:1.0, and preferably from about 3.0:1.0 to about 15.0:1.0.

Alkylation reaction conditions include temperatures in the range of about 0° to about 200°F., and preferably from about 30° to about 110°F. In view of the fact that the alkylation reaction is highly exothermic, suitable means for removing heat from the reaction zone is generally provided. In general practice, the reaction zone is designed such that it functions as a heat-exchanger. A cooling medium is introduced into the reaction zone and indirectly contacts the reaction mixture therein. The quantity of cooling medium is controlled in direct response to the reaction zone temperature. While such a basic technique admittedly offers some form of temperature control, it is clearly susceptible to a large cycling range. In effect, this technique maintains the reaction zone temperature above a predetermined minimum and below the predetermined maximum, the latter to avoid polymerization reactions which adversely affect ultimate product quality.

Alkylation pressures are sufficiently high to maintain the hydrocarbon feed stream and hydrogen fluoride catalyst in substantially liquid phase; that is, from about 15 psig. to about 600 psig. The contact time in the alkylation reaction zone is most conveniently expressed in terms of a space-time relationship which is defined as the volume of catalyst within the reactor or contacting zone, divided by the volume rate per minute of hydrocarbon reactants charged to the zone. Usually, the space-time relationship will be less than about 5 minutes and preferably less than about 2 minutes.

The product effluent from the alkylation reaction zone is introduced into a separation zone generally comprising a two-vessel stacked system. The reaction mixture is introduced into the lower vessel which serves as a vertical mixer, or soaking zone. The mixer is sized and designed to provide an average residence time in the range of about 60 seconds to about 1200 seconds, depending upon the composition of the mixture being charged to the mixer-settler. After the desired residence time has been attained, the effluent is introduced into the upper vessel which serves as a settler to provide a hydrocarbon stream substantially free from the major portion of hydrogen fluoride, and settled hydrogen fluoride substantially free from the major proportion of hydrocarbons. In accordance with a relatively recent technique, at least a portion of the reaction zone effluent is emulsified and recycled to the alkylation reaction zone. The settled hydrogen fluoride is recycled to the reaction zone in admixture with regenerated hydrogen fluoride. The reaction zone effluent generally contains a relatively minor proportion of polymer products formed during the alkylation reaction, notwithstanding temperature control of the reaction mixture within the reaction zone. In order to prevent the build-up of polymer products within the system, a relatively minor proportion of the settled hydrogen fluoride phase, containing polymer products, is introduced into an acid regenerator. Recovered hydrogen fluoride is recycled to the alkylation reaction zone in admixture with the settled hydrogen fluoride.

The hydrocarbon phase separated in the settler vessel is introduced into an isostripper fractionating column for the recovery of the normally liquid alkylate product as a bottoms streams. Propane, unreacted isobutane and a minor quantity of hydrogen fluoride catalyst are removed as an overhead stream and introduced into a settling zone from which the hydrogen fluoride is recycled to the reaction zone. The hydrocarbon phase from this settler is introduced into a depropanizing column with isobutane being removed as a bottoms fraction and recycled in part to the reaction zone and in part to the acid-regenerator for the purpose of stripping hydrogen fluoride from the polymer products which are removed as a bottoms phase. A principally vaporous phase, predominantly propane and containing a minor quantity of hydrogen fluoride is introduced into a hydrogen fluoride stripping column. The hydrogen fluoride is removed as an overhead fraction and introduced into the isostripper settler for ultimate return to the reaction zone. Propane is normally removed from the bottom of the hydrogen fluoride stripper and sent to storage, after being subjected to both alumina treating and potassium hydroxide treating to remove trace quantities of hydrogen fluoride. Similarly, although the normally liquid alkylate product is generally recovered substantially free from hydrogen fluoride, cautious operating techniques dictate that the same be subjected to similar treatments to remove trace quantities of hydrogen fluoride.

The foregoing is representative of a typical hydrogen fluoride-catalyzed alkylation process. As previously stated, the present invention is intended for integration into such a unit for the purpose of achieving a greater degree of efficiency with respect to reaction zone temperature control accompanied by an enhancement of the steady-state operation of the entire system. As a general rule, the character of the olefinic feed stream to an HF alkylation unit is dependent upon the operation of other processes in the refinery. Since these other processes are subject to their own peculiar operating parameters, the composition of the olefinic feed stream is constantly changing. This contributes a particular problem with respect to temperature control of the alkylation reaction mixture. Considering only propylene, 1-butene, 2-butene and isobutylene, as hereinbefore stated, the normally liquid alkylate product quality is improved by increasing the reaction temperature, with respect to 1-butene, and decreasing the temperature of the reaction mixture with respect to 2-butene, or isobutylene. This difficulty is further compounded by virtue of the fact that a higher quality alkylate product results from a propylene feed stream processed at higher temperatures than those which are considered optimum for the alkylation of $C_4$-olefins.

In accordance with the present control system, a hydrocarbon analyzer receives a sample of the olefinic feed stream, introduced into the alkylation reaction zone, and develops a process output signal representative of, and responsive to a composition characteristic of the sample. Another process output signal, representative of and responsive to a composition characteristic of the separated liquid alkylate product, is developed by a second hydrocarbon analyzer. Temperature-sensing means, including an Indicator-Transmitter, senses a reaction zone temperature and develops a process output signal in response thereto. These process output signals are transmitted to computer/comparator means which generates a computer output signal in response to, and as a function of the process output signals and transmits the same to flow-varying means which adjusts the quantity of cooling medium introduced into the reaction zone.

Although the reaction zone temperature may be sensed internally, through the use of a suitable thermowell, a more convenient location is the effluent outlet conduit as close to the reaction vessel as possible. This temperature will be virtually the same as the maximum temperature experienced within the reaction vessel as a result of the exothermicity of the alkylation reaction.

Complete details of the hydrocarbon analyzer, intended for utilization as an essential element of the present control system, in developing a signal representative of a composition characteristic of the alkylate product, may be obtained upon reference to U.S. Pat. No. 3,463,613 (Cl. 23–230). As stated therein, a composition characteristic of a hydrocarbon sample can be determined by burning the same in a combustion tube under conditions which generate a stabilized cool flame. The position of the flame front is automatically detected and utilized to develop a signal which, in turn, is employed to vary a combustion parameter, such as combustion pressure, induction zone temperature or air flow, in a manner which immobilizes the flame front regardless of changes in the composition characteristics of the hydrocarbon sample. The change in the combustion parameter, required to immobilize the flame following a change of sample composition, is correlatable with the composition characteristic change. An appropriate readout device, connecting therewith, may be calibrated in terms of the desired identifying characteristic as, for example, the octane rating.

The hydrocarbon analyzer is conveniently identified as comprising a stabilized cool flame generator with a servo-positioned flame front. The type of analysis effected thereby is not a compound-by-compound analysis such as presented by instruments including mass spectrometers, or vapor phase chromatographs. On the contrary, the analysis is represented by a continuous output signal which is responsive to and indicative of hydrocarbon composition and, more specifically, is correlatable with one or more conventional identifications or specifications of petroleum products such as Reid vapor pressure, ASTM or Engler distillations, or, for motor fuels, anti-knock characteristics such as research octane number, motor octane number or a composite of such octane numbers. The hydrocarbon analyzer used herein receives a hydrocarbon sample containing predominantly gasoline boiling range components, and the output signal of which provides a direct measure of octane number. For brevity, this hydrocarbon analyzer is herein referred to as an "octane monitor".

The composition characteristic of the mixed olefinic feed stream, for which the second hydrocarbon analyzer developers a process output signal, should be correlatable with the relative concentrations of $C_3$- and $C_4$- olefins present in the feed stream. Preferably, the output signal will correlate the concentration of propylene, 1-butene, 2-butene and isobutylene. Therefore, the analyzer may be selected to determine the density of the feed stream, the boiling point thereof, or the propylene concentration directly. Suitable analyzers include, therefore, mass spectrometers and chromatographic columns, the latter either gas-solid, or gas-liquid. As an example, one boiling point monitor constitutes an analytical device which utilizes a modified gas-liquid chromatographic column to determine continuously the boiling characteristics of a process stream. This procedure is based upon the fundamental principle that if elution times are held constant, then, by fixing the starting temperature and programmed heat rate of the column, a fixed-time interval following sample injection will always represent the same boiling temperature. The sample is flashed into a carrier gas (helium) and thence injected into the gas-liquid column. The chromatographic column impedes the passage of the materials in the sample of a function of their boiling points and carbon-chain lengths, the latter, of course, being related to boiling point. As the carrier gas leaves the column and enters the detector, it carries sample components sequenced according to their respective boiling points.

The computer output signal is generated and transmitted to the signal-receiving means, or flow control means, to reset the set point thereof in response to successive comparisons of the composition characteristic. The flow control means in turn transmits the signal to flow-varying means, whereby the flow of the cooling medium is adjusted in response thereto. Second comparator means can be included within the control system for comparing the actual value of the composition characteristic with previously determined deviation limits and for generating an adjustment signal in response to this comparison. When the value lies beyond the specified limits, and the rate of change with respect to time indicates that the value will continue to depart from such limits, the second comparator means will generate an adjustment signal to alter the rate of change.

In further describing my invention, reference will be made to the accompanying drawing which is presented for the sole purpose of describing a typical prior art HF alkylation process havng integrated therein the control system of the present invention. In the drawing, the process is presented by means of a simplified flow diagram in which details such as pumps, instrumentation and other controls, quench systems, heat-exchange and heat-recovery circuits, valving, start-up lines and similar hardware have been eliminated as non-essential to an understanding of the techniques involved. The use of such miscellaneous appurtenances, to modify the process as illustrated, will be evident to those possessing the requisite skill in the art of petroleum refining technology.

DESCRIPTION OF DRAWING

The drawing will be described in conjunction with a commercially-scaled unit designed for the alkylation of isobutane with a mixed olefin feed, containing propylene, butylenes and amylenes, in an exchanger-type reaction vessel. The olefinic hydrocarbon stream, in the amount of about 8,907 Bbl./day, enters the process via line 1; makeup isobutane is introduced via line 3; and, field butane, in the amount of 1,500 Bbl./day is introduced into the system via line 20 and isostripper 19, the isobutane-rich portion thereof being recycled by way of line 2 to combine with the olefinic hydrocarbon and make-up isobutane mixture in line 1. From these fresh feed charge streams, it is desired to produce a full boiling range, normally liquid alkylate product having a Reid vapor pressure of about 10.0 pounds and a clear octane rating of about 93.0; it is further intended to recover LPG grade (liquefied petroleum gas) propane, as well as a normal butane concentrate which is transported to storage.

With specific reference now to the drawing, 8,907 Bbl./day of the olefinic feed stream (1,437.24 moles/hour), is introduced into the process through line 1, and is admixed with 81,051 Bbl./day (11,549.61 moles/hour) of an isobutane-rich recycle stream in line 2, containing 174.14 moles of HF acid, and 3,985 Bbl./day (564.93 moles/hour) of make-up isobutane (95.0% by volume) from line 3, the mixture continuing through line 1 into alkylation reactor 4. The reactor is designed to function as a heat-exchanger having multiple feed injection points, which design is well known and not, therefore, illustrated herein. Hydrogen fluoride, in an amount of 143,585 Bbl./day (88,164.75 moles/hour), is recycled from settler 13 into reactor 4 by way of line 5. This stream is inclusive of 276.18 moles/hour of regenerated acid from line 6, also containing 483.13 moles/hour of an isobutane-rich stream, and 174.14 moles/hour of settled HF acid recovered in line 7 as hereinafter described. In reactor 4, the isobutane/olefinic hydrocarbon mole ratio is about 13.0:1.0 and the HF acid/hydrocarbon volumetric ratio is about 1.48:1.0. Reactor 4 is maintained at a pressure of about 23 psig., with the HF acid and reactant streams being introduced therein at a temperature of about 100°F. The material balance around reaction zone 4, exclusive of the HF acid stream, is presented in the following TABLE I, with the concentrations of the various components being given in terms of moles per hour for convenience.

TABLE I:

| Component | Reaction Zone Material Balance Charge | Effluent |
|---|---|---|
| Ethane | 1.50 | 1.50 |

TABLE I:-continued

| Component | Reaction Zone Material Balance Charge | Effluent |
|---|---|---|
| Propylene | 441.18 | — |
| Propane | 948.31 | 974.53 |
| Butylenes | 416.40 | — |
| Isobutane | 11,206.85 | 10,322.63 |
| N-Butane | 821.63 | 829.34 |
| Amylenes | 4.49 | — |
| Isopentane | 130.74 | 160.68 |
| N-Pentane | 0.96 | — |
| Hexane-plus | 61.50 | 880.15 |
| Polymer Products | — | 0.28 |

As hereinbefore set forth, HF alkylation of an isoparaffin/olefin reactant mixture is highly exothermic, and must be tempered through the use of a cooling medium. In the illustration, the exothermic heat of reaction is removed through the use of 13,028 gallons/minute of water (about 85°F.) entering via line 9, and exiting via line 8 at a temperature of about 90°F. The total reaction product effluent is withdrawn through line 10 at a temperature of about 100°F. and a pressure of about 218 psig.

The product effluent continues through line 10 into mixer/soaker 11, wherein it is maintained for an effective residence time of about 8 minutes. After this holding period, the product effluent is transferred via line 12 into HF acid settler 13. Settled HF acid is removed via line 14 in the amount of 143,019 Bbl./day (87,816 moles/hour), at a pressure of about 203 psig. Of this amount, 142,569 Bbl./day (87,540 moles/hour) are diverted through line 5 as acid recycle to reactor 4. Generally, the remaining 450 Bbl./day (276.45 moles/hour) is accumulated until a sufficient quantity is available for introduction into acid regenerator 15. For the purpose of simplifying the present illustration, it will be presumed that the 276.45 moles/hour of HF (inclusive of polymer products) continues through line 14 into regenerator 15. Regenerator 15 functions at a bottom pressure of about 155 psig., a bottom temperature of about 350°F., a top pressure of about 145 psig. and a top temperature of about 160°F. HF acid is stripped from polymer products by the introduction, via line 16, of an isobutane-rich stream (344.85 moles/hour), at a temperature of 450°F. and pressure of 160 psig. Polymer products, in the amount of 5.3 Bbl./day (0.28 moles/hour) are recovered through line 17, at a pressure of about 155 psig, and a temperature of about 350°F. A portion of the isobutane-rich stream from line 16 is diverted through line 32 in the amount of 138.28 moles/hour, cooled to a temperature of about 100°F., and introduced as reflux into acid regenerator 15. The overhead stream in line 6, comprising 483.13 moles/hour of hydrocarbons and 276.18 moles/hour of regenerated HF acid, is recycled to combine with the settled acid in line 5, and returned to reactor 4. The material balance with respect to acid regenerator 15 is presented in the following TABLE II:

TABLE II:

| Component | Acid Regenerator Material Balance Line Number | | | | |
|---|---|---|---|---|---|
| | 14 | 32 | 16 | 6 | 17 |
| Ethane | — | — | — | — | — |
| Propylene | — | — | — | — | — |
| Propane | — | 1.63 | 10.50 | 12.13 | — |
| Butylenes | — | — | — | — | — |
| Isobutane | — | 127.83 | 323.09 | 450.91 | — |
| N-Butane | — | 7.98 | 10.49 | 18.46 | — |
| Amylenes | — | — | — | — | — |

TABLE II:-continued

| Component | Acid Regenerator Material Balance Line Number | | | | |
|---|---|---|---|---|---|
| | 14 | 32 | 16 | 6 | 17 |
| Isopentane | — | 0.84 | 0.78 | 1.61 | — |
| N-Pentane | — | — | — | — | — |
| Hexane-plus | — | — | — | — | — |
| HF Acid | 276.18 | — | — | 276.18 | — |
| Polymers | 0.28 | — | — | — | 0.28 |

The hydrocarbon-rich phase from settler 13, at a temperature of about 100°F. and a pressure of about 203 psig. is withdrawn through line 18, and consists of 13,168.81 moles/hour of hydrocarbons and 345.78 moles/hour of HF acid. This material is heated to a temperature of about 170°F., and introduced into isostripper 19 at a pressure of about 152 psig. Field butane, at a temperature of about 100°F., enters the upper section of isostripper 19 through line 20, in an amount of 216.24 moles/hour. A normal butane-rich stream, in the amount of 144.89 moles/hour, is recovered as a side-cut via line 21, and is subjected to treatment with potassium hydroxide for the removal of trace quantities of HF acid. Isostripper 19 functions at a bottom temperature of about 371°F., a bottom pressure of about 160 psig., a top temperature of about 140°F. and a top pressure of about 152 psig. The normally liquid alkylate product is recovered through line 22 in an amount of 9,639 Bbl./day (942.45 moles/hour), and is also subjected to caustic treating for acid removal. An isobutane-rich stream, in the amount of 11,208.33 moles/hour, including 31.93 moles/hour of a pump flush stream (not illustrated) from depropanizer 27 is recycled via lines 2 and 1 to reactor 4. Also recovered in line 2 is HF acid in the amount of 174.14 moles/hour. Overhead vapors, consisting of 2,242.63 moles/hour of hydrocarbons and 196.38 moles/hour of HF acid, are withdrawn through line 23. Of this amount, 1,121.31 moles/hour of hydrocarbons and 22.25 moles/hour of HF are used as reflux to isostripper 19; the composition of the hydrocarbon phase is 1.48 moles of ethane, 270.65 moles of propane, 804.75 moles of isobutane, 40.49 moles of n-butane and 3.96 moles of isopentane. The component composition of the various charge and effluent streams, exclusive of HF acid, are presented in the following TABLES III and IV:

TABLE III:

| Component | Isostripper Feed Streams | |
|---|---|---|
| | Line 18 | Line 20 |
| Ethane | 1.50 | — |
| Propylene | — | — |
| Propane | 974.53 | 5.04 |
| Butylenes | — | — |
| Isobutane | 10,322.63 | 101.78 |
| N-Butane | 828.29 | 105.61 |
| Amylenes | — | — |
| Isopentane | 160.68 | 2.46 |
| N-Pentane | — | 1.35 |
| Hexane-plus | 880.15 | — |

TABLE IV:

| Component | Isostripper Effluent Streams | | | |
|---|---|---|---|---|
| | Line 23 | Line 2 | Line 21 | Line 22 |
| Ethane | 2.98 | — | — | — |
| Propylene | — | — | — | — |
| Propane | 546.18 | 670.65 | — | — |
| Butylenes | — | — | — | — |
| Isobutane | 1605.10 | 9644.65 | 6.99 | 1.90 |
| N-Butane | 80.50 | 679.82 | 135.33 | 81.63 |

TABLE IV:-continued

| Component | Isostripper Effluent Streams | | | |
|---|---|---|---|---|
| | Line 23 | Line 2 | Line 21 | Line 22 |
| Amylenes | — | — | — | — |
| Isopentane | 7.86 | 117.96 | 2.46 | 39.01 |
| N-Pentane | — | — | — | 1.13 |
| Hexane-plus | — | 61.50 | 0.10 | 818.55 |

A portion of the overhead from line 23 is diverted as reflux to the top of isostripper 19; this portion consists of 1,121.31 moles/hour of hydrocarbons and 22.25 moles/hour of HF. The remainder is admixed with 22.83 moles/hour of HF from line 24, and is introduced into settler 25.

Settled acid, in the amount of 174.14 moles/hour, is recycled to reactor 4 by way of lines 7 and 5. Hydrocarbons, in the amount of 1,142.55 moles/hour, and HF acid, in the amount of 22.83 moles/hour, are introduced via line 26 into depropanizer 27. A propane concentrate containing 22.83 moles/hour of HF acid is recovered as an overhead stream in line 28, being introduced thereby into HF stripper 29. The bottom stream, 877.55 moles/hour is withdrawn through line 30 and utilized as follows: 53.20 moles/hour are employed as a pump flush stream (not illustrated); 483.13 moles/hour are diverted through line 16 for use in acid regenerator 15; and, 341.28 moles/hour continue through line 30 for recycle to reactor 4 via line 2. Depropanizer 27 functions with a bottom pressure of about 315 psig., a bottom temperature of about 220°F., a top temperature of about 140°F. and a top pressure of about 305 psig. The material balance for depropanizer 27 is presented in the following TABLE V: Hydrogen fluoride, in an amount of about 22.83 moles/hour is withdrawn as an overhead stream in line 24, and admixed with the isostripper overhead in line 23.

TABLE V:

| Component | Depropanizer Material Balance | | |
|---|---|---|---|
| | Line 26 | Line 28 | Line 30 |
| Ethane | 1.50 | 1.50 | — |
| Propane | 275.79 | 259.04 | 16.75 |
| Isobutane | 820.03 | 4.45 | 815.56 |
| N-Butane | 41.25 | — | 41.25 |
| Isopentane | 4.04 | — | 4.04 |

The 264.99 moles/hour of hydrocarbons are recovered via line 31. HF stripper 29 functions with a top temperature of about 140°F., and a pressure of about 310 psig. and a bottoms temperature of 150°F., and a pressure of about 320 psig.

The normally liquid alkylate product withdrawn via line 22 has a Reid Vapor Pressure of 9.9 lbs., a clear octane rating of 93.3 (research method), 104.2 with 3.0 cc. of tetraethyl lead, and a gravity of 74.6 °API. The results of a 100-ml. ASTM distillation is presented in the following TABLE VI:

TABLE VI:

| Alkylate Product ASTM Distillation | |
|---|---|
| Volume Percent | °F. |
| Initial Boiling Point | 92 |
| 5.0% | 119 |
| 10.0% | 136 |
| 20.0% | 170 |
| 30.0% | 196 |
| 40.0% | 206 |
| 50.0% | 212 |
| 60.0% | 218 |
| 70.0% | 223 |

TABLE VI:-continued

| Alkylate Product ASTM Distillation Volume Percent | °F. |
|---|---|
| 80.0% | 234 |
| 90.0% | 273 |
| 95.0% | — |
| End Boiling Point | 356 |

Octane monitor 41 is field-installed adjacent isostripper 19; it utilizes a stabilized cool flame generator having a servo-positioned flame front. The flow of oxidizer (air) and fuel (alkylate product effluent from line 22) are fixed, as is the induction zone temperature. Combustion pressure is the parameter which is varied in such a manner that the stabilized cool flame front is immobilized. Upon experiencing and detecting a change in a composition characteristic, in this illustration octane number, the change in pressure required to immobilize the flame front within the octane monitor provides a direct indication of the change in the sample delivered to the analyzer's combustion chamber by way of line 33. Typical operating conditions for the octane monitor are: air flow, 3,500 cc./min. (STP); fuel flow, 1.0 cc./min.; induction zone temperatures, Research Octane, 700°F.; induction zone temperature, Motor Octane, 800°F.; combustion pressure, 4.0 to 20.0 psig.; and, octane range (max.), 80 to 102.

The actual calibrated span of the octane monitor as herein employed, will generally be considerably narrower. For example, where the target octane rating is 95.0 Clear (Research Method), a suitable span may be 90–96 research octane. When such a relatively narrow span is employed, the octane number change is essentially directly proportional to the change in combustion pressure. As shown in the drawing, the sample system may comprise a sample loop taking, for example, liquid at a rate of 100 cc./min. via line 33 and returning excess by way of line 34, the sample itself being injected, from an intermediate point at a controlled rate (about 1.0 cc./min.), by a metering pump to the combustion tube of the octane monitor. The octane monitor output signal is transmitted through line 35 to computer/comparator 36.

A sample of the mixed olefinic feed stream in line 1 is withdrawn through line 41 and introduced into analyzer 43, with excess sample being returned through line 42. Analyzer 43 is a gas-liquid chromatographic column functioning as a boiling point monitor. The detector correlates the boiling points with the relative concentrations of propylene, 1-butene, 2-butene and isobutylene in the feed stream. A process output signal representative thereof is transmitted via instrument line 44 to computer/comparator 36. Temperature-sensing means 45 senses the temperature of the alkylation reaction zone effluent in line 10, and transmits an appropriate output signal, via line 46, to Temperature Indicator Transmitter 47. The latter, in turn, transmits the output signal, via instrument line 48 to computer/comparator 36.

Computer/comparator 36 generates a computer output signal in response to, and as a function of the process output signals received via lines 35, 44 and 48, and, therefore, a function of feed composition, reaction zone temperature and alkylate product octane rating. The computer output signal is transmitted, by way of line 37 to controller 38 to reset the setpoint thereof in response thereto. An appropriate adjustment of control valve 40 is made via line 39, either to increase, or decrease the flow rate of the cooling medium in line 9. It is understood, of course, that control valve 40 can be installed in line 8, the cooling medium exit line from reaction zone 4. Since the samples of alkylate product from line 22 and olefin feed from line 1 are taken continuously, and varying output signals continuously transmitted to computer/comparator 36, rapid compensation for the change in olefinic composition is afforded.

Through the utilization of the present control system, a refinery functioning with a mixed olefin feed stream, as the charge to an HF alkylation system, is afforded close control over either a desired target octane rating, or over maximizing the octane rating, regardless of the changes in feed composition.

I claim as my invention:

1. A process for alkylating an isoparaffin with an olefinic feed stream, containing at least two olefins, which process comprises the steps of:
   a. reacting said isoparaffin with said feed stream, in admixture with a hydrogen fluoride catalyst, in an alkylation reaction zone, at alkylating conditions resulting in a reaction product effluent containing normally liquid alkylate;
   b. regulating the temperature of the reaction mixture, within said reaction zone, through indirect contact therein with a cooling medium, the flow of which is adjusted by flow-varying means;
   c. introducing a sample of said olefinic feed stream into a first hydrocarbon analyzer and developing therein a first process output signal representative of a composition characteristic of said olefinic feed stream;
   d. sensing a temperature of said reaction zone and developing a second process output signal representative thereof;
   e. recovering said normally liquid alkylate from said product effluent;
   f. introducing a sample of said alkylate into a second hydrocarbon analyzer and developing therein a liquid process output signal representative of a composition characteristic of said sample;
   g. transmitting said three process output signals to computer/comparator means and developing therein a computer output signal in response to, and as a function of said three process output signals; and,
   h. transmitting said computer output signal to said flow-varying means, whereby the flow of said cooling medium is adjusted in response thereto.

2. The process of claim 1 further characterized in that said olefinic feed stream contains at least two olefins having from 3 to about 11 carbon atoms per molecule.

3. The process of claim 1 further characterized in that said isoparaffin contains from about 4 to about 7 carbon atoms per molecule.

4. The process of claim 2 further characterized in that said olefinic feed stream contains at least two olefins selected from the group consisting of propylene, 1-butene, 2-butene and isobutylene.

5. The process of claim 3 further characterized in that said isoparaffin is isobutane.

6. The process of claim 1 further characterized in that said alkylating conditions include an isoparaffin/olefin molar ratio in the range of about 1.1:1.0 to about 20.0:1.0 and a reaction zone temperature from about 30° to about 200°F.

* * * * *